US007550270B2

(12) United States Patent
Kroll et al.

(10) Patent No.: US 7,550,270 B2
(45) Date of Patent: Jun. 23, 2009

(54) ILEITIS DIAGNOSTIC ASSAY

(75) Inventors: Jeremy J. Kroll, Urbandale, IA (US); Michael B. Roof, Ames, IA (US); Marc A. Eichmeyer, Bondurant, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 75 days.

(21) Appl. No.: 10/918,006

(22) Filed: Aug. 13, 2004

(65) Prior Publication Data

US 2006/0035287 A1 Feb. 16, 2006

(51) Int. Cl.
*G01N 33/554* (2006.01)
(52) U.S. Cl. ............... 435/7.32; 435/7.92; 435/101; 435/7.1; 536/123.1; 424/234.1
(58) Field of Classification Search ........... 435/7.1, 435/7.32, 7.92, 101; 536/123.1; 424/234.1
See application file for complete search history.

(56) References Cited

OTHER PUBLICATIONS

Modern Microbiological Methods; Bacterial Cell Surface Techniques; I.C. Hancock and I.R. Poxton; a Wiley-Interscience Publication; 1988 John Wiley & Sons.
The serological response to *Salmonella serovars* typhimurium and infantis in experimentally infected pigs. The time course followed with an indirect anti-LPS ELISA and bacteriological examinations; B. Nielsen, D. Baggesen, F. Bager, J. Haugegaard and P. Lind; Veterinary Microbiology 47 (1995) 205-218.
Immunochemical analyses of serum antibodies from pig herds in *Salmonella* non-endemic region; Camilla Wiuff, Britt-Marie Thorberg, Anders Engvail, and Peter Lind; Veterinary Microbiology 85 (2002) 69-82.
Validation of an immunoperoxidase monolayer assay as a serologic test for porcine proliferative enteropathy; Roberto M. C. Guedes, Connie J. Gebhart, John Deen, Nathan L. Winkelman; J Vet Diagn Invest 14:528-530(2002).
Enzyme-Linked Immunosorbent Assay for Measuring Ileal Symbiont Intracellularis-Specific Immunoglobulin G Response in Sera of Pigs; P.K. Holyoake, R.S. Cutler, I.W. Caple, and R.P. Monckton; Journal of Clinical Microbiology, Aug. 1994, p. 1980-1985.
Evaluation of antemortem polymerase chain reaction and serologic methods for detection of *Lawsonia* intracellularis-exposed pigs; Jeffrey P. Knittel, MS; Dianna M. Jordan, DVM, MS; Kent J. Schwartz, DVM, MS; Bruce H. Janke, DVM, PhD; Michael B. Roof, PhD; Steven McOrist, PhD, DVM; D.L. Harris, DVM, PhD; AJVR, vol. 59, No. 6, Jun. 1998, pp. 722, 723, 725.
Lipopolysaccharide-Based Enzyme-Linked Immunosorbent Assay for Experimental Use in Detection of Antibodies to *Lawsonia intracellularis* in Pigs; Kroll, Eichmeyer, Schaeffer, McOrist, Harris, and Roof; Clinical and Diagnostic Laboratory Immunology, Jun. 2005, vol. 12, No. 6; p. 693-699.
Development, characterization and diagnostic application of a monoclonal antibody specific for a proteinase K resistant *Lawsonia intracellularis* antigen; Boesen, Jensen, Jungersen, Riber, Boye, and Moller; Veterinary Microbiology 105 (2005) p. 199-206.
Evaluation of a novel enzyme-linked immunosorbent assay for serological diagnosis of porcine proliferative enteropathy; Boesen, Jensen, Moler, Nielsen, and Jungersen; Veterinary Microbilogy 109 (2005) p. 105-112.

*Primary Examiner*—Jennifer E Graser
(74) *Attorney, Agent, or Firm*—Michael P. Morris; Mary-Ellen M. Devlin

(57) ABSTRACT

Improved immunoassays for the protection of antibodies against *Lawsonia intracellularis* are provided which permit rapid, easy detection of low concentrations of anti-*Lawsonia* antibodies in animal-derived specimens. The preferred assay is an ELISA assay employing an antigenic extract of *L. intracellularis* lipopolysaccharide.

30 Claims, No Drawings

ILEITIS DIAGNOSTIC ASSAY

BACKGROUND OF THE INVENTION

1. Field of the Invention

The present invention is broadly concerned with improved immunoassays for the detection of antibodies against *Lawsonia intracellularis*, as well as an effective antigen comprising and preferably consisting essentially of an antigenic extract of *L. intracellularis* lipopolysaccharide. The preferred assay is an indirect-type ELISA assay having excellent specificity and sensitivity, allowing use of the assay for detection of low levels of antibody in animal-derived specimens during initial stages of infection prior to the onset of clinical signs of disease.

2. Description of the Prior Art

Porcine proliferative enteritis (PPE), known as ileitis, intestinal adenomatosis, or necrotic enteritis, is a naturally occurring disease that can affect pigs from waning to young adult stage. PPE was formerly believed to be caused by a camplyobacter-like organism or ileal symbiont intracellularis. More recently, it has been established that the causative agent is *Lawsonia intracellularis*, an obligate intracellular, gram-negative bacterium. The disease is of economic importance owing to death loss, increased medication costs, poor weight gain and decreased food conversion in affected animals.

A key element in the rational therapy and effective control of PPE is a rapid and accurate identification of etiologic agents. PPE may be diagnosed by observation of gross lesions and is confirmed by observation of specific hystopathological lesions in which the intracellular curved rods are demonstrated by special staining methods incorporating the use of an anti-*Lawsonia* monoclonal antibody. Ideally, a final determination should be made through the isolation of the causative agent. However, the isolation and culture of *L. intracellularis* requires specialized cell culture techniques.

Attempts have been made in the past to develop rapid assays for the detection of anti-*Lawsonia* antibodies. Current serological-based assays such as indirect fluorescence antibody test (IFAT) and immuno-peroxidase assay (IPMA) demonstrate good sensitivity and specificity in the detection of anti-*Lawsonia* antibodies antemortem in pig serum. Knittel J P, Jordan D M, Schwartz J K, et al. *Evaluation of Antemorten Polymerase Chain Reaction and Serological Methods for Detection of Lawsonia Intracellularis-exposed Pigs*. American Journal of Veterinarian Research. 59:722-726 (1998). Guedes R M C, Gebhart C J, Deen J, et al. *Validation of an Immunopreoxidase Monolayer Assay as a Serological Test for Porcine Proliferative Enteropathy*. Journal of Veterinary Diagnostic Investigation. 14:528-530(2002), the teachings and content of these references are hereby incorporated by reference. However, neither of these assays is sensitive enough to detect the lower concentrations of anti-*Lawsonia* antibodies often found in pig serum during the initial exposure and onset of infection time periods. In addition, these prior assays rely on highly skilled technicians to accurately conduct the tests and interpret the results, e.g., the results are subjectively obtained by spending many hours looking into a microscope, analyzing wells illuminated by UV or natural light, searching for *L. intracellularis* or *L. intracellularis*-infected cells stained fluorescent green or red representing a "positive" sample.

Enzyme-linked immunoassays (ELISA) have also been developed for detection of anti-*Lawsonia* antibodies. These prior efforts failed to produce a sufficiently sensitive and specific assay owing to various limitations including poor antigen quality and quantity, variability in antibody titers, overlapping antibody titer between infected and non-infected pigs lack of a valid positive/negative "cut-off" value, and cross-reactivity of pig antibodies to non-specific antigen components. Holyoake P K, Cutler R S, Caple I W, Monckton R P. *Enzyme-linked Immunosorbent Assay for Measuring Ileal Symbiont Intracellularis-specific Immunoglobulin G Response in Sera in Pigs*. Journal of Clinical Microbiology. 31: 1980-1985 (1994), the teachings and content of which is hereby incorporated by reference.

There is accordingly a need in the art for an improved anti-*Lawsonia* antibody assay which is highly sensitive and specific, permitting accurate detection of low concentrations of antibodies in animal-derived specimens during the early stages of infection.

Lipopolysaccharides (LPS) are a major suprastructure of gram-negative bacteria such as *L. intracellularis* which contributes greatly to the structural integrity of the bacteria, and protects them from host immune defenses. LPS's form a part of the Gram negative bacteria cell wall and comprise three parts: polysaccharide side chains, core polysaccharides and lipid A. Lipid A may contain unusual fatty acids (e.g., hydroxy-mysteric acids) while core polysaccharides often contain unusual sugars (e.g., KDO, keto-deoxyoctulonate and heptulose). The polysaccharide side chain is referred to as the O-antigen of the bacteria. LPS's function as endotoxin, because they can bind to the CD14 receptor of macrophage, triggering the whole cascade for macrophage/endothelial cells to secrete pro-inflammatory cytokines.

SUMMARY OF THE INVENTION

The present invention overcomes the problems outlined above and provides an improved immunoassay for detecting the presence of antibodies against *Lawsonia intracellularis* with a high degree of specificity and sensitivity, allowing the assay to be used for the early detection of PPE. Broadly speaking, the assay of the invention is an immunoassay wherein an animal-derived specimen is contacted with an effective amount of an antigen comprising at least a portion of a lipopolysaccharide of *L. intracellularis*, causing the formation of complexes between the antigen and the antibodies, and then determining the presence of such antibodies. In preferred forms, the assay is an indirect ELISA test.

The animal-derived specimen is most preferably sera, but can also include colostrums, joint fluids, salivas, tissue homogenates and feces. These specimens can be prepared in accordance with conventional techniques for assay purposes. Although the invention is particularly concerned with detection of PPE in swine, analogous *Lawsonia*-caused diseases can also be detected in animals such as pigs, hamsters, blue fox, emus, deer, dogs, guinea pigs, horses, rhesus macaque monkeys, ostriches, rabbits and rats. The antibodies detected using the methods of the invention generally are selected from the group consisting of IgG, IgA and IgM antibodies.

The preferred antigen for use in the immunoassays of the invention is a portion or extract of a lipopolysaccharide of *L. intracellularis*. This extract preferably has a molecular weight of from about 15-25 kDa, more preferably from about 18-20 kDa. The extract or portions thereof should be of sufficient size and antigenicity to induce an immune response in the animal upon administration of an effective amount of the antigen. Furthermore, the extract or portion thereof must be of sufficient size for antibody-antigen complexes with LPS antibodies. In particularly preferred forms, the LPS antigen exhibits an endotoxicity of from about 3-75 EU/ml (more preferably from about 10-60 EU/ml, still more preferably from about 20-50, and even more preferably from about 25-40 EU/ml) using the bacteria endotoxin test. The antigen preferably consists essentially of LPS abtract, and good results have been obtained with an extract of *L. intracellularis* ATCC Accession No. PTA-4927, deposited on Jan. 9, 2003, with the ATCC, 10801 University Blvd., Manassas Va. 20110-2209. PTA-4927 was tested by the ATCC on Apr. 21, 2004 and was found to be viable. The date of conversion to the Budapest Treaty was Oct. 16, 2007.

The most preferred ELISA is a indirect-type assay and involves first coating the wells of a microtiter plate with LPS, followed by overnight incubation at room temperature. A blocking agent is then added with further overnight incubation at 4° C. The selected dilute detection antibody is then added with incubation at 37° C. for one hour, followed by diluted conjugate with further one hour (37° C.) incubation. Next, the TMB chromagen is added with incubation at room temperature for five minutes. At this point the reaction is stopped with the addition of 2M sulfuric acid and the plate is read at 450 nm.

The preferred ELISA test is optimized in the case of a starting LPS extract sample of ATCC Accession No. PTA-4927 having an endotoxin level of about 34.75 EU/ml. In such an instance, the antigen should be present at a dilution of from about 1:250 to 1:8000, more preferably from about 1:400 to 1:6000, still more preferably from about 1:500 to 1:4000, even more preverably from about 1:600 to 1:3000, still more preferably from about 1:750 to 1:2000, even more preferably from about 1:900 to 1:1500, with 1:1,000 being optimum. The detection antibody should be present at a dilution level of about 1:20-1:320, 1:25-1:240, 1:30-1:128, 1:35-1:60 with 1:40 being the best. The ELISA conjugate should be used at a level of from about 1:250-1:2000, 1:300-1:1500, 1:350-1:1000, 1:400-1:600, with 1:500 being preferred. Of course, appropriate dilution levels may be readily calculated if the starting antigen has a different endotoxin level than the preferred product of the invention.

The present invention also lends itself to recombinant LPS antigens being used as the antigenic source. In such instances, the LPS antigen or portion thereof will be generated using conventional recombinant techniques. For example, DNA encoding for the LPS antigen or desired portion thereof can be inserted expression invectors and operably linked to expression control sequences which then permit the expression vector to express the desired LPS antigen or portion thereof. The expressed antigen is then recovered and used in accordance with the present invention. Of course, those of skill in the art are familiar with various ways of producing and recovering recombinant antigens in accordance with the present invention. In all instances, recombinant antigens in accordance with the present invention will preferentially bind to or hybridize with *L. intracellularis* antibodies.

DESCRIPTION OF THE PREFERRED EMBODIMENTS

The following examples set forth presently preferred techniques for constructing and using *Lawsonia* LPS as an antigenic source for immunoassays. Such examples include an indirect-type ELISA immunoassay against *Lawsonia* antibodies. It is to be understood, however, that such examples are provided by a way of illustration only, and nothing therein should be construed as a limitation upon the overall scope of the invention.

EXAMPLE I

Development and Confirmation of LPS-Based Indirect ELISA Assay

Bacterial Antigen Preparation

The bacterial isolate was identified as high passage (>20 passages past initial isolation from the affected gut) *L. intracellularis* isolate #15540 (ATTC Accession No. PTA-4927). This isolate was acquired from a Danish sow affected with acute hemorrhagic proliferative enteropathy (HPE), as confirmed by routine histology and immunohistochemistry (IHC) staining techniques and co-cultured to obtain a pure culture of *L. intracellularis* by methods previously described. Lawson G H K, McOrist S, Jasni, et al. *Intracellular Bacteria of Porcine Proliferative Enteropathy: Cultivation and Maintenance in Vitro*. Journal of Clinical Microbiology. 31:1136-1142 (1993), the teachings and content of which are incorporated by reference herein. Multiple 30 L batches of *L. intracellularis* #15540 were propagated using fresh McCoy cell (ATCC #1696) suspensions in bioreactors (Applicon, Inc., Foster City, Calif.). Active cultures were allowed to reach 80-100% cell infectivity and then harvested by centrifugation using an Avanti Beckman J-20I centrifuge (Beckman Instruments, Inc., Fullerton, Calif.), JA-10 rotor at 17,000×g for 15 minutes at 4° C. The supernatants of each batch were discarded and cell pellets containing both extracellular *L. intracellularis* and McCoy cells infected with *L. intracellularis* were resuspended in 30 ml sterile 1× phosphate-buffered saline (PBS) and stored at −80° C.

In order to purify *L. intracellularis* from McCoy cells, a discontinuous percoll gradient was prepared following methods previously described with slight modifications. Holyoake P K, Cutler R S, Caple I W, Monckton R P. *Enzyme-linked Immunosorbent Assay for Measuring Ileal Symbiont Intracellularis-specific Immunoglobulin G Response in Sera in Pigs*. Journal of Clinical Microbiology. 31:1980-1985 (1994), the teachings and content of which are hereby incorporated by reference. Briefly, 225 ml of percoll (Amersham Biosciences, Pharmacia Biotech, Uppsala, Sweden) was mixed with 260 ml of reagent grade (RG) water and 15 ml of 5M sodium chloride (NaCl, Fisher Brand). Harvested cultures mentioned above were passed >20 times through a 25 gauge needle and 5 ml of bacterial/McCoy cell homogenate was transferred to 25 ml of the percoll gradient into 30 ml polycarbonate centrifuge tubes. Tubes were mixed by inversion and centrifuged at 37,000×g for 1 h at 4° C. The ensuing suspension contained scattered cellular debris in the upper 50% of the tube while one distinct cellular banding pattern was visualized at a buoyant density of 1.075 g/ml. The upper half of the gradients were removed while the bands were carefully collected using a 5 ml polypropylene pipette and transferred to new 30 ml centrifuge tubes containing 20 ml of sterile PBS. The tubes were centrifuged (Avanti Beckman J-20I, JA-17 rotor) at 37,000×g for 15 minutes at 4° C. and the process repeated a maximum of 3 times to wash out the percoll from each sample. After the final centrifugation step, the pellets were resuspended in 1 to 2 ml of sterile PBS, pooled, aliquoted into 1.8 ml cryovial tubes (Nalgene, Nalgene Nunc Int'l., Rochester, N.Y.) and stored at −80° C. A sample of the resuspension containing highly concentrated, percoll purified *L. intracellularis* #15540 was observed under dark field microscopy to confirm presence of tiny curved rods and absence of intact McCoy cells. The LPS antigenic component was extracted from the percoll purified *L. intracellularis* #15540 antigen with hot aqueous phenol using methods previously described with slight modifications. Westphal, O. and Luderitz, O. *Chemische Erforschung von Lipopolysacchariden Gramnegativer Bacterien.* Angew. Chemical 66: 407-17 (1954), the content and teaching of which are hereby incorporated by reference. Briefly, 18 ml of percoll purified *L. intracellularis* and 3.75 ml of phenol chloroform (Ameresco, Solon, Ohio), pH 8.0 was incubated separately in a 65° C. water bath for 10 minutes. After the initial incubation period, 4.5 ml of the percoll purified *L. intracellularis* was transferred to each tube containing 0.9375 ml of hot phenol chloroform and gently mixed by inversion. Tubes were incubated for an additional 25 minutes in the 65° C. water bath, mixing by inversion every 5 minutes during incubation and then cooled overnight at 4° C. Slight phase separation of aqueous and solid phases occurred in each tube during cold storage. Each tube was centrifuged (Avanti Beckman J-20I, JA-17 rotor) at 7,700×g for 25 minutes at 4° C. and the LPS-containing supernatant from all 4 tubes was pooled and retained while the cell pellets were discarded. The supernatant was transferred to pre-sterilized dialysis tubing (Spectrum Laboratories, Inc., Rancho Domingo, Calif.), placed in a 4 L plastic beaker and dialyzed in cold reagent grade (reverse osmosis) water for 24 to 48 hours to remove the phenol chloroform from the sample. The reagent grade water was exchanged with fresh water every 2 to 4 hours until the washing step was complete. The resultant purified *L. intracellularis* LPS extract was carefully collected and stored at −80° C. until use.

Confirmation of the LPS extract was visualized through separation on 4-12% Bis-Tris pre-cast gel (NuPAGE, Invitrogen, Carlsbad, Calif.) by sodium dodecyl sulfate polyacrylamide gel electrophoresis (SDS-PAGE) in MOPS running buffer (NuPAGE, Invitrogen). The LPS extract was compared to percoll purified whole-cell *L. intracellularis* and uninfected whole-cell McCoy cells. Samples were prepared for SDS-PAGE by diluting each 1:2 into 4× lithium salt dodecyl sulfate (LDS) denaturing buffer (NuPAGE, Invitrogen) and incubated in a 85° C. water bath for 10 minutes. The gel was periodate silver stained following procedures outlined by Bio-Rad Silver Stain instructions with modifications. In brief, the gel was subjected to a primary fixation in 40% Methanol (MeOH, Fisher Brand, Hanover Park, Ill.)/10% acetic acid (Fisher Brand) (v/v) for 20 to 30 minutes followed by incubation in 40% MeOH/10% acetic acid (v/v) containing 0.7% periodic acid for an additional 5 minutes at room temperature. A secondary fixation involved transferring the gel into 10% ethanol (EtOH)/5% acetic acid (v/v) for 5 minutes followed by oxidation in oxidizer reagent (Bio-Rad, Hercules, Calif.) for 5 minutes then, washed in deionized water until the yellow color was gone from the gel. The gel was incubated in 0.16 mM dithiothreitol (DTT) in water for 5 minutes and stained in silver reagent (Bio-Rad) for 20 minutes at Room temperature. The gel was washed once in deionized water for 20 to 40 seconds and placed in developing reagent (Bio-Rad) until the desired strength of banding appeared. The reaction was stopped in 5% (v/v) acetic acid for 20 minutes at room temperature and washed once in deionized water. Proteins were identified by their molecular mass using a 10 to 220 kDa protein marker (BenchMark, Invitrogen).

LPS-Based Indirect ELISA

Anti-*Lawsonia* immunoglobulin G (IgG) antibodies were detected in test samples using an *L. intracellularis* LPS-based indirect enzyme linked immunosorbent assay (LPS-ELISA). *Lawsonia intracellularis* LPS was coated at 100 μl/well on Immulon 2HB plates (Dynex, Chantilly, Va.) at a 1:1000 dilution in 0.05M sodium carbonate coating buffer, pH 9.6, sealed with mylar plate sealers (Thermo Labsystems, Franklin, Mass.) and incubated at Room temperature for 24 hours. Each plate was washed using the Ultrawash PLUS (Dynex), 350 ml/well, zero soak time, for 1 wash cycle with wash buffer containing 0.05% Tween 20 (Fisher Brand), 0.137M NaCl (Fisher Brand), 0.005M potassium chloride (KCl, Sigma, St. Louis, Mo.), 0.009M Sodium Phosphate, diabasic ($Na_2HPO_4$, Sigma), 0.001M potassium phosphate ($KH_2PO_4$, Sigma), pH 7.2 to 7.4, in RG water. Antigen-coated plates were blocked at 300 ml/well with blocking buffer containing 5% (v/v) non-fat dried milk (Bio-Rad) in SeaBlock™ (Pierce Biotech, Rockford, Ill., containing steelhead salmon serum and 0.1% sodium oxide in PBS) at 4° C. for 24 hours to prevent non-specific binding of test sera to the plates. Each plate was then washed for 3 cycles as mentioned above. Test sera and controls were pre-diluted 1:40 in blocking buffer.

Fifty microliters per well of diluted sera was transferred to each plate in duplicate, sealed and incubated at 37° C. for 1 hour. The washing steps were repeated for 3 cycles before adding 50 μl/well of a 1:500 dilution of goat anti-swine IgG horseradish peroxidase (HRP) conjugate (Kirkegaard and Perry Laboratories, Inc., Gaithersburg, Md.) in blocking buffer. Plates were sealed and incubated at 37° C. for 1 hour. The washing steps were repeated for 3 more cycles and then, 50 μl/well of peroxidase substrate consisting of a 2-component 3,3',5,5' tetramethylbenzidine (TMB, KPL) was applied to each plate and incubated at Room temperature for 5 minutes. This was done to observe the presence of antigen-antibody complexes within each test sample. The colorimetric reaction was stopped by transferring 50 μl/well of 2M sulfuric acid ($H_2SO_4$, Fisher Brand) solution. Plates were read at 450 nm wavelength on a V-max 96-well microtiter plate reader (Medtechs, Inc., Chapel Hill, N.C.) to obtain optical density (OD) values for each test sample. Standard controls containing a range of high positive to low positive (by serial two-fold dilution of the highly positive sample in blocking buffer) and negative antibodies against the *L. intracellularis* LPS extract were included in each plate. The test plates were considered valid if the coefficient of determination ($r^2$-value) was $^3$ 0.9 in a linear regression analysis of the standard's OD values. An empty well not containing test or control samples served as a blank control for all tests.

Validation of LPS-ELISA

Porcine sera were obtained from the following studies for use in validating the LPS-ELISA for detection of anti-*Lawsonia* IgG antibodies in pigs. (i) Two pigs approximately 3 weeks of age were hyperimmunized by intramuscular injection with 2 ml of *L. intracellularis* LPS extract formulated 1:2 with Freund's incomplete adjuvant (Sigma). One pig approximately 3 weeks of age was given a 2 ml intramuscular injection of placebo consisting of Dulbecco's Minimal Essential Medium (DMEM) with 5% (v/v) bovine serum (JRH Biosciences, Lenexa, Kans.) formulated 1:2 with Freund's incomplete adjuvant. Boosters of each inoculum were administered 3 weeks and 6 weeks post initial inoculation for generation of positive (antibodies to *L. intracellularis* LPS) and negative (no *L. intracellularis* antibodies) control test serum. Four to six milliliters of serum was collected from each pig prior to inoculation, at 3 weeks and 6 weeks post inoculation and tested for reaction of *L. intracellularis* whole cell antigen by an indirect florescent antibody serology test (IFAT), Knittel J P, Jordan D M, Schwartz J K, et al. *Evaluation of Antemorten Polymerase Chain Reaction and Sero-* logic Methods for Detection of Lawsonia Intracellularis-exposed Pigs. American Journal of Veterinarian Research. 59:722-726 (1998), the teachings and content of which are hereby incorporated by reference, to confirm presence or absence of anti-*Lawsonia* antibodies in serum samples. At 8 weeks post-initial inoculation, animals were euthanised and a final serum collection was obtained. The positive control serum from each pig was pooled, tested to confirm positive reaction to *L. intracellularis* by IFAT, and both anti-*Lawsonia* LPS positive and negative control serum was stored in 1 ml aliquots at −80° C.

Porcine sera from 2 previously conducted vaccine efficacy studies, Kroll, J., et al. (2004). Evaluation of protective immunity in pigs following oral administration of an avirulent live vaccine of *Lawsonia intracellularis*. AJVR 65(5): 559-565, the teaching and content of which is hereby incorporated by reference, were tested to investigate an anti-*Lawsonia* LPS antibody positive/negative optical density cut-off limit. Test serum from eighty 6 to 9 week old pigs previously confirmed to be IFAT-positive for anti-*Lawsonia* antibodies were generated after experimental infection with a virulent heterologous *L. intracellularis* isolate N101494 (Boehringer Ingelheim Vetmedica, Inc., St. Joseph, Mo.). Test serum previously confirmed to be IFAT-negative, was collected from eighty 3 to 9 week old strict control pigs that did not receive a vaccination or challenge any time during each clinical study.

175 serum samples were collected from 25 pigs after vaccination with a live attenuated *L. intracellularis* vaccine, Enterisol® Ileitis (Boehringer Ingelheim Vetmedica, Inc.), after challenge with a virulent heterologous *L. intracellularis* isolate N101494 or both. Another 70 serum samples were collected from 10 strict control pigs that did not receive a vaccination or challenge and remained IFAT negative for anti-*Lawsonia* antibodies throughout the study. The study design included thirty five 3 to 4 week old pigs randomly blocked into 3 treatment groups. On day 0 of the study, 15 pigs from group 1 received a 2 ml oral dose of vaccine while groups 2 and 3 (10 pigs/group) received an equivalent dose of placebo consisting of uninfected McCoy cell suspension in growth medium. On day 21, pigs in groups 1 and 2 were given an intragastric dose of virulent heterologous pure culture challenge of *L. intracellularis* N101494. On day 42, pigs were necropsied and evaluated for lesion development to identify efficacy of the vaccinated pigs compared to non-vaccinated, challenged pigs. Fecal samples and serum were collected weekly from day 0 to 42 for routine diagnostic testing to detect rates of exposure and active shedding of *L. intracellularis* due to vaccine or challenge administration. Lesions were evaluated to confirm presence of PE at day 42 only by gross examination, histological and IHC methods as described below.

Confirmation of PE in Pigs

Gross lesions found in the ileum or colon of pigs in clinical studies described above were scored according to the severity of mucosal thickness (1=normal, 2=mild thickening, 3=moderate thickening/inflammation, 4=severe thickening/inflammation/mucosal hemorrhaging or necrosis may be present). Kroll, J., et al. (2004). Evaluation of protective immunity in pigs following oral administration of an avirulent live vaccine of *Lawsonia intracellularis*. AJVR 65(5): 559-565. Samples 2-4 cm in length of ileum and colon were collected post mortem, fixed by immersion in buffered formalin and processed for detection of microscopic lesions. This included Hematoxylin and Eosin (H&E) and IHC staining incorporating specific *L. intracellularis* monoclonal antibodies. Kroll, J., et al., AJVR, (2004). The latter is considered the current standard for assessment of the actual infection status of a pig with *L. intracellularis*. Kroll, J., et al. (2004). Microscopic lesions found in IHC stained tissue were scored separately according to severity of *L. intracellularis* specific cell proliferation (0=normal, 1=mild/focal, 2=moderate/diffuse, 3=severe/diffuse). Average gross and microscopic lesion scores and the frequency of lesions detected in the affected tissue were calculated for group comparisons. Average gross and macroscopic lesion scores were considered the primary parameter for determining vaccine efficacy against virulent heterologous challenge in previous studies. Kroll, J., et al. (2004).

EXAMPLE II

Preferred LPS-ELISA Materials and Methods

The following sets forth the presently preferred LPS-ELISA assay in accordance with the invention.

A. Protocol

1. Materials a. LPS Binding Plates:
  Immunlon 2 HB 96 well plates, Dynex Cat. No. 3455 or equivalent.

b. Dilution Plates:
  Falcon Pro-Bind Assay Plate (Fisher Scientific, Pittsburg, Pa.), 96-well, U-Bottom without lid (polystyrene, non-sterile), Becton Dickinson (San Diego, Calif.) Cat. No. 353910 or equivalent.

c. Plate Sealers:
  Mylar Plate Sealer, Thermo Labsystems (Franklin, Mass.) Cat. No. 5701 or equivalent.

d. Coating Buffer:
  0.05M Sodium Carbonate buffer
    10.6 g $Na_2CO_3$ Sigma Cat. No. S6139 or equivalent.
    QS with reagent grade (RG) $H_2O$ (or equivalent) to 1.0 L.
    pH=9.6±0.1
    Store at 2-7° C. until use.
    Expiry: 7 days.

e. Wash Solution:
  0.05% Tween 20, 0.137M NaCl, 0.005M KCl, 0.009M $Na_2HPO_4$, 0.001M $KH_2PO_4$
    32.0 g NaCl.
    0.8 g KCl.
    2.44 g $Na_2HPO_4$.
    0.8 g $KH_2PO_4$.
    QS with RG $H_2O$ or equivalent to 4.0 L.
    pH to 7.2-7.4 with NaOH or HCl.
    2.0 ml of Tween, Fisher Cat No. BP337-100 or equivalent.
    Store at room temperature (25±5° C.) until use.
    Expiry: 1 week.

f. Blocking Solution:
  5% Non-fat dry milk in Seablock™.
    25.0 g Non-fat dry milk. Bio-Rad Cat No. 170-6404 or equivalent.
    QS to 500 mL with Seablock™. Pierce Biotech Cat. No. 37527 or equivalent.
    Store at 2-7° C. until use.
    Expiry: 1 month.

g. Antigen:
  1:1000 dilution of lipopolysaccharide whole molecules from *L. intracellularis*.
    40 µl *L. intracellularis* LPS into 40 ml of coating buffer.
    Use immediately.

h. Detection Antibody:
   1:40 dilution of convalescent pig serum antibodies to *L. intracellularis*.
      3 µl pig serum or equivalent into 120 µl of blocking solution.
      Store at 2-7° C. until use.
      Expiry: 24 hours.
i. Conjugate antibody:
   1:500 dilution of Goat anti-mouse IgG (H+L)—Horse Radish Peroxidase (HRP). Kierkegaard and Perry Laboratories, Inc. Cat. No. 14-14-06 or equivalent.
      40 µl conjugate into 20 ml of blocking solution.
      Store at 2-7° C. until use.
      Expiry: 24 hours.
j. Substrate:
   Two-Component Microwell Peroxidase Substrate (Gaithersburg, Md.). KPL Cat No. 50-76-00 or equivalent.
      Mix equal volumes of TMB Peroxidase Substrate (Reagent A) with Peroxidase Solution B (Reagent B) immediately prior to use.
      Volume required=5 mL/plate. Therefore, 2.5 mL of Reagent A+2.5 mL of Reagent B for 1 test plate.
      Store at 2-7° C. until use.
      Expiry: Pre-mixed reagents per manufacturer's suggested expiration date. Use mixed substrate solution immediately.
k. Stop Solution:
   2M $H_2SO_4$.
      In a fume hood, carefully mix: 444.4 mL of RG $H_2O$. 55.6 mL of 18M $H_2SO_4$ Fisher Cat No. A300c-212, or equivalent.
      Store at room temperature until use.
      Expiry: 6 months.
l. Positive Control
   1:2,564 dilution of hyperimmunized pig serum containing anti-*Lawsonia* LPS IgG antibodies.
      3.9 µl of positive control Lot #090203 into 10 ml of blocking solution
      Store at 2-7° C. until use.
      Expiry: 24 hours
m. Negative Control
   1:2,564 dilution of hyperimmunized pig serum containing no antibodies against *L. intracellularis* LPS molecules.
      3.9 µl of positive control Lot #090203 into 10 ml of blocking solution
      Store at 2-7° C. until use.
      Expiry: 24 hours
2. Methods
a. Samples are run in duplicate. Number of plates needed=Total number of samples/40 samples per plate. Round up to a whole number of plates. Columns 11 and 12 will contain 1:10 serial dilutions of negative and positive control serum.
b. Dilute *L. intracellularis* LPS antigen 1:1000 or appropriate working dilution in coating buffer. Volume required=Number of plates×10 ml/plate.
c. Add 100 ml of diluted antigen to every well of each plate.
d. Seal plates with plate sealers and incubate at room temperature overnight (14-24 hours).
e. Wash plates with wash solution using Dynex Ultrawash PLUS, 350 ml/well, zero soak time, for 1 wash cycle. Tap plates dry on paper towels.
f. Add 300 ml of block solution to all wells. Seal plates and incubate at 2-7° C. overnight (14-24 hours).
g. Wash plates with wash solution using Dynex Ultrawash PLUS, 350 µl/well, zero soak time, for 3 wash cycles. Tap plates dry on paper towels.
h. In a U-bottom dilution plate, add 120 µl of blocking solution sample to wells in columns 1-10 and wells B-H in columns 11 and 12.
i. Add 240 µl of negative and positive controls in wells of row A in columns 11 and 12 respectively.
j. Make 10-fold dilutions of each control serum by transferring 120 µl of diluted control in wells A-11 and A-12 to wells B-11 and B-12 using a 50-300 µl multi-channel pipette, taking care not to transfer diluted negative control to the last well of column 11 (well H-11) as this sample will serve as a plate blank.
k. Dilute detection antibody (convalescent pig sera) 1:40 in blocking solution by transferring 3 µl of sample into 120 µl of blocking solution in each well of the dilution plate. Dilute by adding a different sample each time to wells A-1, B-1, C-1, etc.
l. Using a 50-300 µl multichannel pipette, mix the contents in column 1 by pipetting up and down at least 3 times and transfer 50 µl/well to columns 1 and 2 of the antigen coated LPS-binding test plates. Change tips and repeat step until all diluted samples have been transferred in duplicate across the plate.
m. Transfer 50 µl/well of the negative control (wells A-H, column 11) to corresponding wells of the test plate(s). Repeat step for the positive control. Each control contains enough diluted sample to use in 2 test plates.
n. Seal test plate(s) with plate sealers and incubate for 1.0 hour±15 minutes at 37° C.±2.0° C.
o. Wash plates with wash solution using Dynex Ultrawash PLUS, 350 µl/well, zero soak time, for 3 wash cycles. Tap plates dry on paper towels.
p. Add 50 µl of conjugate antibody diluted 1:500 or appropriate working dilution to all wells of the test plate(s). Volume required=Number of plates×5 ml/plate.
q. Seal test plate(s) with plate sealers and incubate for 1.0 hour±15 minutes at 37° C.±2.0° C.
r. Wash plates with wash solution using Dynex Ultrawash PLUS, 350 µl/well, zero soak time, for 3 wash cycles. Tap plates dry on paper towels.
s. Add 50 µl of substrate to use to all wells of the test plate(s), incubate at room temperature for five minutes±1 minute.
t. Stop the reaction with the addition of 50 µl of Stop solution to all wells five minutes after the addition of substrate.
u. Read plates on a plate reader equipped with a 450 nm wavelength filter.
3. Interpretation of Results
a. Test samples exhibiting >0.200 optical density at 450 nm wavelength are considered positive for anti-*Lawsonia* LPS IgG antibodies.
b. Test samples exhibiting <0.200 optical density at 450 nm wavelength are considered negative for anti-*Lawsonia* LPS IgG antibodies.

We claim:

1. An immunoassay for detecting the presence of antibodies against *Lawsonia intracellularis* in an animal-derived specimen comprising the steps of contacting said specimen with an effective amount of an antigen comprising at least a portion of an isolated lipopolysaccharide of *Lawsonia intracellularis*, said portion being of sufficient size to form antibody-antigen complexes with *Lawsonia intracellularis* LPS antibodies and having an endotoxicity of about 3-75 EU/ml, causing the formation of complexes between said antigen and said antibodies, and determining the presence of said complexes, wherein the presence of said complexes indicates the presence of said antibodies.

2. The immunoassay of claim 1, said specimen selected from the group consisting of animal-derived sera, colostrums, joint fluids, salivas, tissue homogenates, and feces.

3. The immunoassay of claim 1, said animal selected from the group consisting of pigs, hamsters, blue fox, emus, deer, dogs, guinea pigs, horses, rhesus macaque monkeys, ostriches, rabbits and rats.

4. The immunoassay of claim 1, said antibodies being selected from the group consisting of IgG, IgA and IgM antibodies.

5. The immunoassay of claim 1, said immunoassay being an ELISA test.

6. The immunoassay of claim 5, said antigen being recombinantly derived.

7. The immunoassay of claim 5, said ELISA test including the steps of immobilizing said antigen on a surface, contacting said specimen with said immobilized antigen, causing a complex between antibodies in said specimen and said antigen, and detecting said complexes.

8. The immunoassay of claim 1, said lipopolysaccharide having a molecular weight of from about 15-25 kDa.

9. The immunoassay of claim 8, said molecular weight being from about 18-20 kDa.

10. The immunoassay of claim 1, said antigen capable of inducing an immune response in said animal upon administration of an effective amount of the antigen to the animal.

11. The immunoassay of claim 1, said endotoxicity being from about 25-40 EU/ml.

12. The immunoassay of claim 1, said antigen comprising an isolated lipopolysaccharide extract from the strain deposited as ATCC Accession No. PTA-4927.

13. An antigen for detecting the presence of antibodies against *Lawsonia intracellularis*, said antigen comprising at least a portion of an isolated *Lawsonia intracellularis* lipopolysaccharide, said portion being sufficient size to form antibody-antigen complexes with *Lawsonia intracellularis* LPS antibodies and having an endotoxicity of about 3-75 EU/ml.

14. The antigen of claim 13, said lipopolysaccharide having a molecular weight of from about 15-25 kDa.

15. The antigen of claim 14, said molecular weight being from about 18-20 kDa.

16. The antigen of claim 14, said antigen capable of inducing an immune response in said animal upon administration of an effective amount of the antigen to the animal.

17. The antigen of claim 14, said lipopolysaccharide being recombinantly derived.

18. The antigen of claim 14, said endotoxicity being from about 25-40 EU/ml.

19. The antigen of claim 13, said antigen comprising an isolated lipopolysaccharide extract from the strain deposited as ATCC Accession No. PTA-4927.

20. In an enzyme-linked immunoassay for detecting the presence of antibodies against *Lawsonia intracellularis* in an animal-derived specimen, the improvement which comprises employing an isolated lipopolysaccharide of *Lawsonia intracellularis* having an endotoxicity of about 3-75 EU/ml, as an antigen in said immunoassay.

21. The immunoassay of claim 20, said specimen selected from the group consisting of animal-derived sera, colostrums, joint fluids, salivas, tissue homogenates, and feces.

22. The immunoassay of claim 20, said animal selected from the group consisting of pigs, hamsters, blue fox, emus, deer, dogs, guinea pigs, horses, rhesus macaque monkeys, ostriches, rabbits and rats.

23. The immunoassay of claim 20, said antibodies being selected from the group consisting of IgG, IgA and IgM antibodies.

24. The immunoassay of claim 20, said ELISA test being an indirect-ELISA test.

25. The immunoassay of claim 24, said ELISA test including the steps of immobilizing said antigen on a surface, contacting said specimen with said immobilized antigen, causing a complex between antibodies in said specimen and said antigen, and detecting said complexes.

26. The immunoassay of claim 20, said lipopolysaccharide having a molecular weight of from about 15-25 kDa.

27. The immunoassay of claim 26, said molecular weight being from about 18-20 kDa.

28. The immunoassay of claim 20, said antigen capable of inducing an immune response in said animal upon administration of an effective amount of the antigen to the animal.

29. The immunoassay of claim 20, said endotoxicity being from about 25-40 EU/ml.

30. The immunoassay of claim 20, said antigen comprising an isolated lipopolysaccharide extract from the strain deposited as ATCC Accession No. PTA-4927.

* * * * *